United States Patent
Beck et al.

(10) Patent No.: US 7,103,578 B2
(45) Date of Patent: Sep. 5, 2006

(54) REMOTE MEDICAL DEVICE ACCESS

(75) Inventors: Timothy L. Beck, Pendleton, IN (US); Morris J. Young, Indianapolis, IN (US); Ronald W. Peyton, deceased, late of Indianapolis, IN (US); by Amy Peyton, legal representative, Indianapolis, IN (US); Robert Meek, Indianapolis, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 591 days.

(21) Appl. No.: 09/866,260

(22) Filed: May 25, 2001

(65) Prior Publication Data
US 2002/0178126 A1 Nov. 28, 2002

(51) Int. Cl.
G06T 17/60 (2006.01)

(52) U.S. Cl. ............... 705/75; 705/1; 434/236; 600/300; 128/920

(58) Field of Classification Search ............... 705/75, 705/1; 434/236; 600/300; 128/920
See application file for complete search history.

(56) References Cited

U.S. PATENT DOCUMENTS

| | | | |
|---|---|---|---|
| 5,307,263 A | 4/1994 | Brown | |
| 5,371,687 A | 12/1994 | Holmes, II et al. | |
| 5,416,695 A | 5/1995 | Stutman et al. | |
| 5,421,343 A | 6/1995 | Feng | |
| 5,434,611 A | 7/1995 | Tamura | |
| 5,544,649 A | 8/1996 | David et al. | |
| 5,558,638 A | 9/1996 | Evers et al. | |
| 5,569,212 A | 10/1996 | Brown | |
| 5,576,952 A | 11/1996 | Stutman et al. | |
| 5,626,144 A | 5/1997 | Tacklind et al. | |
| 5,633,910 A | 5/1997 | Cohen | |
| 5,678,562 A | 10/1997 | Sellers | |
| 5,711,671 A | 1/1998 | Geeslin et al. | |
| 5,720,733 A | 2/1998 | Brown | |
| 5,730,146 A | 3/1998 | Itil et al. | |
| 5,740,800 A | 4/1998 | Hendrickson et al. | |
| 5,752,976 A | 5/1998 | Duffin et al. | |
| 5,782,814 A | 7/1998 | Brown et al. | |
| 5,785,650 A | 7/1998 | Akasaka et al. | |
| 5,791,342 A | 8/1998 | Woodard | |
| 5,792,117 A | 8/1998 | Brown | |
| 5,810,747 A | 9/1998 | Brudny et al. | |
| 5,822,715 A | 10/1998 | Worthington et al. | |
| 5,857,967 A * | 1/1999 | Frid et al. | 600/301 |
| 5,897,493 A | 4/1999 | Brown | |
| 5,899,855 A | 5/1999 | Brown | |

(Continued)

FOREIGN PATENT DOCUMENTS

CA 2125300 11/1995

(Continued)

OTHER PUBLICATIONS

HSRRB Medical Device Review Guidelines; Jul. 2002.*

(Continued)

Primary Examiner—James P. Trammell
Assistant Examiner—John M. Winter
(74) Attorney, Agent, or Firm—Sujatha Subramaniam; Roche Diagnostics Operations, Inc.

(57) ABSTRACT

Systems, client computing devices, server computing devices, and methods are disclosed for accessing medical devices, providing remote access to medical devices and/or remotely accessing medical devices. In one exemplary embodiment, client computing devices utilize protocol components that may be obtained from a server computing device via a network to communicate with medical devices in a communications protocol supported by the medical device.

6 Claims, 5 Drawing Sheets

U.S. PATENT DOCUMENTS

| | | |
|---|---|---|
| 5,936,539 A | 8/1999 | Fuchs |
| 5,942,986 A | 8/1999 | Shabot et al. |
| 5,944,659 A | 8/1999 | Flach et al. |
| 5,956,501 A | 9/1999 | Brown |
| 5,959,529 A | 9/1999 | Kail, IV |
| 5,960,403 A | 9/1999 | Brown |
| 5,974,124 A | 10/1999 | Schlueter, Jr. et al. |
| 5,974,262 A | 10/1999 | Fuller et al. |
| 5,993,001 A | 11/1999 | Bursell et al. |
| 5,997,476 A | 12/1999 | Brown |
| 6,014,581 A | 1/2000 | Whayne et al. |
| 6,017,307 A | 1/2000 | Raines |
| 6,023,585 A | 2/2000 | Perlman et al. |
| 6,024,699 A | 2/2000 | Surwit et al. |
| 6,032,119 A | 2/2000 | Brown et al. |
| 6,039,251 A | 3/2000 | Holowko et al. |
| 6,083,248 A * | 7/2000 | Thompson ............... 607/30 |
| 6,110,148 A | 8/2000 | Brown et al. |
| 6,113,578 A | 9/2000 | Brown |
| 6,134,504 A | 10/2000 | Douglas et al. |
| 6,135,949 A | 10/2000 | Russo et al. |
| 6,144,922 A | 11/2000 | Douglas et al. |
| 6,161,095 A | 12/2000 | Brown |
| 6,167,362 A | 12/2000 | Brown et al. |
| 6,168,563 B1 | 1/2001 | Brown |
| 6,196,970 B1 | 3/2001 | Brown |
| 6,233,539 B1 | 5/2001 | Brown |
| 6,248,065 B1 | 6/2001 | Brown |
| 6,270,455 B1 | 8/2001 | Brown |
| 6,270,457 B1 * | 8/2001 | Bardy ............... 600/300 |
| 6,277,071 B1 | 8/2001 | Hennessy et al. |
| 6,283,761 B1 * | 9/2001 | Joao ............... 434/236 |
| 6,311,163 B1 | 10/2001 | Sheehan et al. |
| 6,352,523 B1 | 3/2002 | Brown et al. |
| 6,379,301 B1 | 4/2002 | Worthington et al. |
| 6,401,085 B1 | 6/2002 | Gershman et al. |
| 6,424,996 B1 | 7/2002 | Killcommons et al. |
| 6,442,432 B1 | 8/2002 | Lee |
| 6,612,984 B1 * | 9/2003 | Kerr, II ............... 600/300 |
| 2001/0031997 A1 | 10/2001 | Lee |
| 2001/0037060 A1 | 11/2001 | Thompson et al. |
| 2001/0056328 A1 | 12/2001 | Trippel et al. |
| 2002/0026223 A1 | 2/2002 | Riff et al. |

FOREIGN PATENT DOCUMENTS

| | | |
|---|---|---|
| EP | 1 164 530 | 12/2001 |
| WO | WO 98/24212 | 6/1998 |
| WO | WO 98 24212 A | 6/1998 |
| WO | WO 98/24358 | 6/1998 |
| WO | WO 98/59487 | 12/1998 |
| WO | WO 99/04043 | 1/1999 |
| WO | WO 99/23597 | 5/1999 |
| WO | WO 00 07013 | 2/2000 |
| WO | WO 00/07013 | 2/2000 |
| WO | WO 00/25192 | 5/2000 |
| WO | WO 00/25496 | 5/2000 |
| WO | WO 00 25496 A | 5/2000 |
| WO | WO 00/29983 | 5/2000 |
| WO | WO 00/32088 | 6/2000 |
| WO | WO 00/32098 | 6/2000 |
| WO | WO 00/33231 | 6/2000 |
| WO | WO 00/33232 A2 | 6/2000 |
| WO | WO 00/49549 | 8/2000 |
| WO | WO 00/54170 | 9/2000 |
| WO | WO 00/54205 | 9/2000 |
| WO | WO 00/54206 | 9/2000 |
| WO | WO 00/72181 | 11/2000 |
| WO | WO 01/47600 | 7/2001 |
| WO | WO 01/48675 | 7/2001 |
| WO | WO 01/48676 | 7/2001 |
| WO | WO 01/59570 | 8/2001 |
| WO | WO 01/69505 | 9/2001 |
| WO | WO 02/21317 | 3/2002 |
| WO | WO 02/25551 | 3/2002 |
| WO | WO 02/41227 | 5/2002 |

OTHER PUBLICATIONS

"Can Getting Started with Your Can Hardware and the Ni-Can Software for Windows 95" [Online] Jan. 1998, National Instruments Corporate Headquarters, Austin, TX, USA Retrieved from the Internet: URL:pcitco25.cem.ch/SI/lvbv/can/321371c.pdf [retrieved on Sep. 25, 2002].

* cited by examiner

REMOTE MEDICAL DEVICE ACCESS

FIELD OF THE INVENTION

The present invention relates generally to medical devices, and more particularly to remote medical device access.

BACKGROUND OF THE INVENTION

Patients commonly use medical devices to monitor various biological and/or physiological conditions. For example, patients with diabetes often utilize a blood glucose meter to monitor their blood glucose levels periodically. However, medical devices are also used for monitoring and/or analyzing biological/physiological parameters or conditions such as body fluids or bodily functions (e.g. blood, urine, saliva), bodily signals (e.g. electrocardio-signals, brain waves, blood pressure waves), and/or other bodily stimuli (e.g. respiration) to obtain measurements of blood pressure, blood gases, blood coagulation, electrolytes, cardiovascular activity, drug levels, respiration rate, stress, etc. These medical devices often store measurement data which may be retrieved, archived, and/or analyzed. Physicians, nurses, technicians, and patients typically find such measurement data useful in assessing the patient's health, in assessing the effectiveness of medications and other treatments, and in adjusting a patient's current treatment regime to obtain better health for the patient.

To facilitate retrieval of data, the above medical devices typically include a communications port which allows communication with another device such as a computer. Furthermore, the medical devices are often implemented such that a computing device may control the medical device and adjust various operating parameters via the communications port. However, in order to retrieve the data from the medical device, control the medical device, and/or adjust various operating parameters of the medical device via the communications port, the computing device must be configured to communicate with the medical device via a communications protocol designed for the specific medical device.

SUMMARY OF THE INVENTION

Systems, client computing devices, server computing devices, and methods are disclosed for accessing medical device, providing remote access to medical devices, and/or remotely accessing medical devices. In accordance with one embodiment of the present invention, there is provided a method for accessing a medical device operably coupled to a computing device. One step of the method includes receiving identification information from the computing device that is indicative of a medical device type. Another step of the method includes transferring a protocol component to the computing device based upon the identification information. The method further includes the step of receiving measurement data from the medical device in response to the computing device communicating with the medical device via the protocol component.

Pursuant to another embodiment of the present invention, there is provided a method of providing a computing device with remote access to a medical device. One step of the method includes providing the computing device with identification information from which a protocol component for use with the medical device is determined. Another step of the method includes receiving the proper protocol component from the computing device in response to providing the computing device with the identification information. The method also includes the step of communicating with the medical device via the proper protocol component.

Pursuant to another embodiment of the present invention, there is provided a first computing device for remotely accessing a medical device operably coupled to a second computing device via a network. The first computing device includes a storage device comprising a plurality of protocol components that configure the second computing device to communicate with a plurality of medical devices in accordance with communications protocols supported by the plurality of medical devices. The first computing device also includes a memory comprising a plurality of instructions, and a network interface adapted to communicate with the second computing device via the network. The first computing device further includes a processor operably coupled to the storage device, the memory, and the network interface. The processor is adapted to execute the plurality of instructions to cause the processor to receive from the second computing device via the network interface identification information from which a medical device type of the medical device coupled to the second computing device is determined. The processor is further adapted to execute the plurality of instructions to cause to provide protocol component information to the second computing device via the network interface which identifies the protocol component from the plurality of protocol components for the second computing device to use to communicate with the medical device. The processor is further adapted to execute the plurality of instructions to cause the processor to receive measurement data from the medical device via the network interface in response to the second computing device communicating with medical device via the protocol component identified by the protocol component information.

Objects, features, and advantages as well as further embodiments will become apparent from the following description and the attached drawings.

DETAILED DESCRIPTION OF EXEMPLARY EMBODIMENTS

Figure 1:
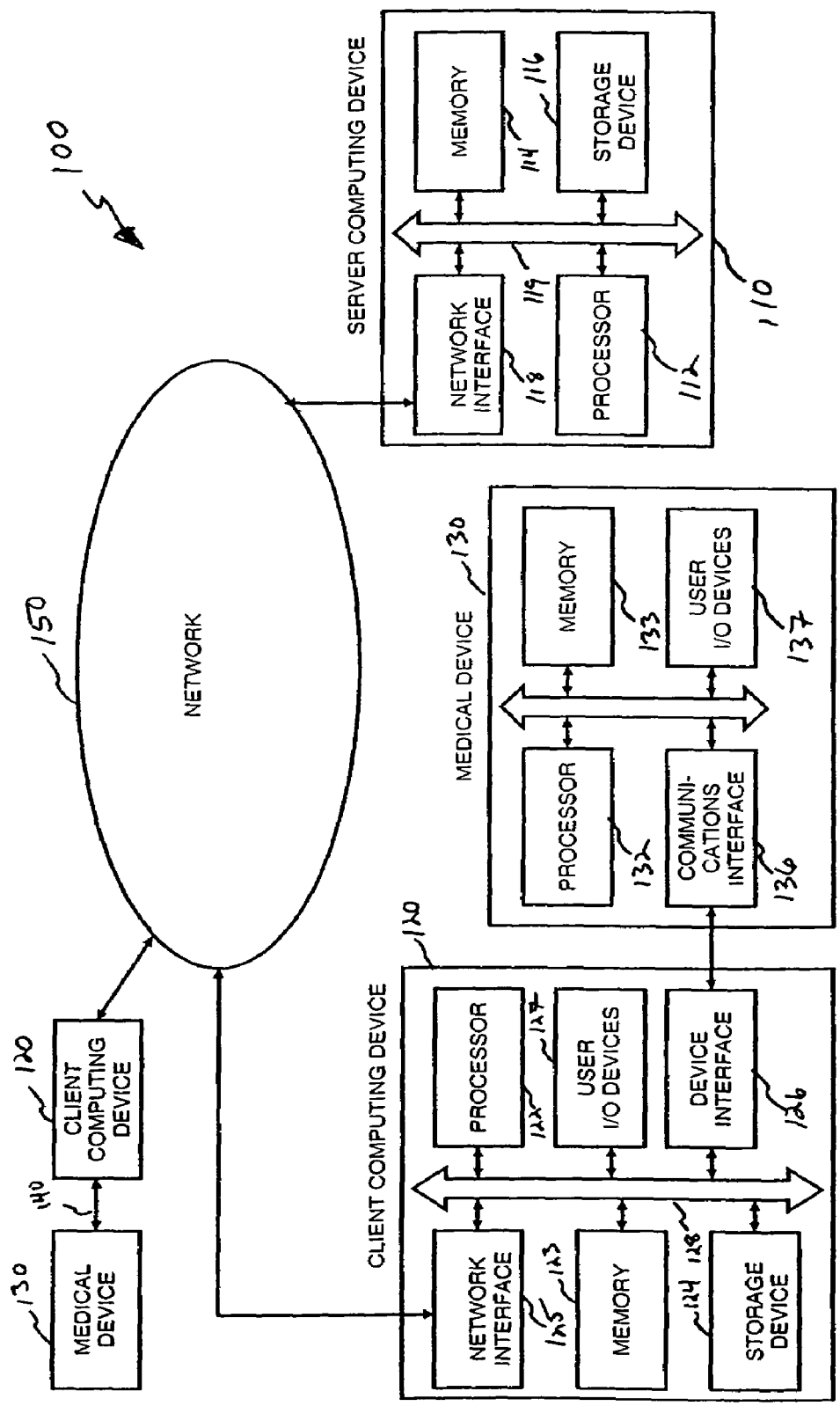
FIG. 1 shows a block diagram of a system which incorporates various features of the present invention therein.

While the invention is susceptible to various modifications and alternative forms, exemplary embodiments thereof have been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 2:
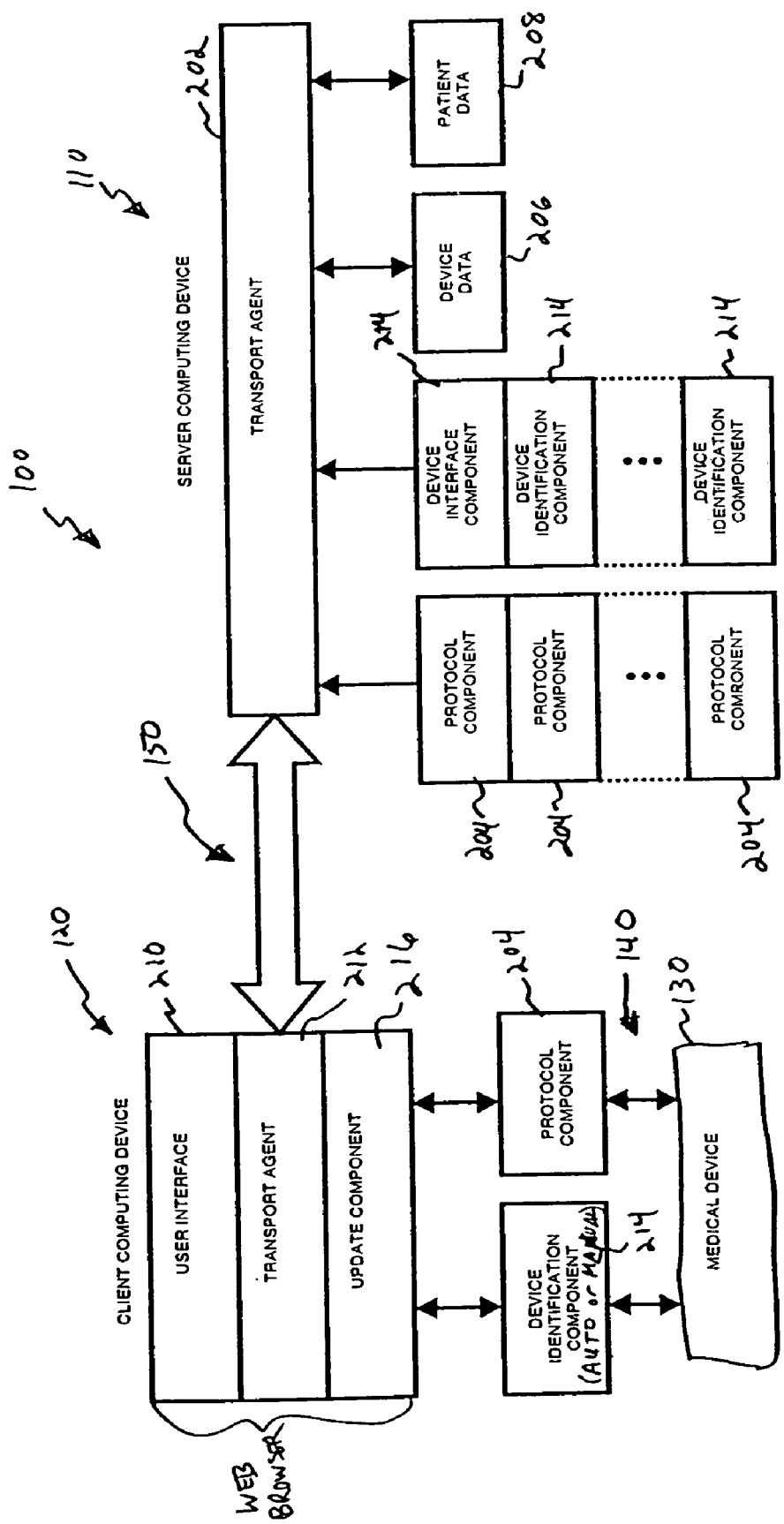
FIG. 2 shows a function block diagram illustrating functional components of the system shown in FIG. 1.

A system 100 is shown in FIG. 1 and FIG. 2 which incorporates various features of the present invention. As illustrated, the system 100 includes a server computing device 110, a client computing device 120, a medical device 130 operable coupled to the client computing device 120 via a communications link 140, and a network 150 which operably couples the client computing device 120 to the server computing device 110. In general, the system 100 automatically or semi-automatically configures the client computing devices 120 for communication with medical devices 130 that utilize different communications protocols, and provides the server computing device 110 remote access to the medical devices 130 via the client computing devices 120 and the network 150.

More specifically, the system 100 comprises a set of protocol components 204 which the server computing device 110 transfers to the client computing devices 120. Each protocol component 204 configures the client computing devices 120 for communication with a specific set of medical device models or types of medical devices 130. The protocol components are illustratively software components which provide a set of rules that govern how the client computing device 120 communicates with a medical device 130. Illustratively, the protocol components specify rules for setting up, carrying out, and terminating a communications connection. The protocol components also specify the format of the information transmitted across the communications connection. More specifically, each protocol component 204 in the exemplary embodiment is adapted to configure the client computing devices 120 to send medical device configuration information, medical device version information, medical device setup information, and medical device measurement data to the server computing device 110. In addition, each protocol component 204 is adapted to configure the client computing devices 120 to send updated configuration information or setup information to the medical device 130.

The server computing device 110 is adapted to detect, over the network 150, medical devices 130 that are operably coupled to the client computing devices 120. Illustratively, the server computing device 110 is adapted to query the connected medical devices 130 for medical device version information, medical device configuration information, medical device setup information, and medical device measurement data. While the server computing device 110 and the client computing device 120 are typically separate computing devices, the server computing device 110 may also function as a client computing device 120. Accordingly, if a medical device 130 is coupled to a server computing device 110 that also provides functionality of the client computing device 120, then information need not be transferred across a network 150.

Now referring to FIG. 1 in more detail, the server computing device 110 of the exemplary system 100 includes a processor 112, memory 114, a storage device 116, a network interface 118, and a system bus 119. The exemplary server computing device 110 as depicted in FIG. 1 is generally illustrative of server computer systems and web servers manufactured by Dell Computer Corporation of Round Rock, Tex., Gateway, Inc. of San Diego, Calif., and Compaq Computer Corporation of Houston, Tex. While the server computing device 110 may be implemented with a server computer system or web server from the above vendors, the server computing device 110 may alternatively, or in addition, include other computing devices such as network server appliances, server farms, server clusters, and/or network accessible storage devices.

The processor 112 of the exemplary server computing device 110 includes a single x86 processor from Intel or AMD. However, the processor 112 may alternatively include one or more processors utilizing very long instruction words, (VLIW) code morphing, complex instruction set computer (CISC), reduced instruction set computer (RISC), single instruction/multiple data (SIMD), multiple instruction/multiple data (MIMD), or other architectures from vendors such as Compaq, National Semiconductor Corporation, Motorola and Transmeta Corporation. The processor 112 is generally operable to execute software and/or firmware routines stored in the memory 114. As a result of executing the software and/or firmware routines of the memory 114, the processor 112 controls the general operation of the server computing device 110. More specifically, the processor 112 as a result of executing software and/or firmware routines of the memory 114 is generally operable to configure the client computing devices 120 for communication with the medical devices 130. Further, the processor 112 as a result of executing the software and/or firmware routines of the memory 114 is generally operable to configure the server computing device 110 to retrieve measurement data from the medical devices 130 via the client computing devices 120, archive measurement data received from the medical devices, process the measurement data received from the medical devices, and/or provide the client computing devices 120 with processed measurement data.

The memory 114 of the exemplary server computing device 110 is operable to store data and instructions used by the processor 112. To this end, the memory 114, in an exemplary embodiment, includes standard random access memory for storing the data and software instructions needed by the processor 112. However, the memory 114 may alternatively include other volatile memory types such as DRAM, SDRAM, and SRAM for storing data and software instructions and/or non-volatile memory such as ROMs, PROMs, EEPROMs, and flash memory for storing data and firmware instructions.

The storage device 116 of the exemplary server computing device 110 is generally operable to store data and/or software instructions of the exemplary server computing device 110. To this end, the storage device 116 may include various computer readable and/or writeable media devices such as hard disk drives, floppy disk drives, CD-ROM drives, DVD-RAM drives, RAID devices, and/or Disk-On Chip devices to name a few. Furthermore, the storage device 116 may store data in a number of different manners such as raw data to the media of the storage device 116, files in a file system of the storage device 116, and/or data, records, or objects in a database of the storage device 116. Moreover, the storage device 116 may include multiple media devices and may be distributed among several computing devices such as other servers of a server farm, other database servers, or other network accessible storage (NAS) devices.

The network interface 118 of the exemplary server computing device 110 generally operably couples the exemplary server computing device 110 to the network 150 such that the server computing device 110 may communicate with the client computing devices 120 that are also operably coupled to the network 150. To this end, the network interface 118 of the exemplary embodiment comprises a network interface controller such as an Ethernet controller or Token Ring controller that connects the server computing device 110 to the network 150 via a local area network, firewall, gateway, and/or router. However, the network interface 118 may alternatively, or in addition, include an analog modem for use over POTS telephone lines such as a 28.8K or 56K modem, or a digital modem such as a Cable modem for use over a cable distribution network, an ISDN modem for use over an ISDN telephone line, or a DSL modem for use over a DSL telephone line.

The system bus 119 of the exemplary server computing device 110 is generally operable to interconnect the processor 112, the memory 114, the storage device 116, and the network interface 118. The system bus 119 in the exemplary embodiment includes an address bus and data bus which enable the various components of the exemplary server computing device 110 to communicate with one another. Furthermore, the system bus 119 may be implemented with one or more buses utilizing one or more bus architectures such as PCI, ISA, and VME.

As can be seen from FIG. 1, the exemplary client computing device 120 includes a processor 122, memory 123, a storage device 124, a network interface 125, a device interface 126, one or more user I/O devices 127, and a system bus 128. The exemplary client computing device 120 as depicted in FIG. 1 is generally illustrative of personal computer systems, desktop computer systems, and/or workstations manufactured by Dell Computer Corporation of Round Rock, Tex., Gateway, Inc. of San Diego, Calif., and Compaq Computer Corporation of Houston, Tex. While the client computing device 120 may be implemented with a personal computer system, desktop computer system, and/or workstation from the above vendors, the client computing device 120 may alternatively, or in addition, include other computing devices such as network enabled (more preferably Internet enabled) computing devices such as handheld computers, laptop computers, set-top boxes, network appliances, and/or gaming consoles.

The processor 122 of the exemplary client computing device 120 includes a single x86 processor from Intel or AMD. However, the processor 122 may alternatively include one or more processors utilizing VLIW, code morphing, CISC, RISC, SIMD, MIMD, or other architectures from vendors such as Compaq, National Semiconductor Corporation, and Transmeta Corporation. As a result of executing the software and/or firmware routines of the memory 123, the processor 122 controls the general operation of the client computing device 120. More specifically, the processor 122 as a result of executing software and/or firmware routines of the memory 123 is generally operable to configure the client computing device 120 for communication with the medical devices 130. Further, the processor 122 as a result of executing the software and/or firmware routines of the memory 123 is generally operable to configure the client computing device 120 to determine the medical device type of a medical device 130 operably coupled thereto, obtain from the server computing device 110 a protocol component 204 (See, FIG. 2.) suited for communicating with the medical device 130 operably coupled thereto, and/or communicate with the medical device 130 via the protocol component 204.

The memory 123 of the exemplary client computing device 120 is operable to store data and instructions used by the processor 122. To this end, the memory 123, in an exemplary embodiment, includes standard random access memory for storing the data and software instructions needed by the processor 122. However, the memory 123 may alternatively include other volatile memory types such as DRAM, SDRAM, and SRAM for storing data and software instructions and/or non-volatile memory such as ROMs, PROMs, EEPROMs, and flash memory for storing data and firmware instructions.

The storage device 124 of the exemplary client computing device 120 is generally operable to store data and/or software instructions of the exemplary client computing device 120. To this end, the storage device 124 may include various computer readable and/or writeable media devices such as hard disk drives, floppy disk drives, CD-ROM drives, DVD-RAM drives, RAID devices, and/or Disk-On Chip devices to name a few. Furthermore, the storage device 124 may store data in a number of different manners such as raw data to the media of the storage device 124, files in a file system of the storage device 124, and/or data, records, or objects in a database of the storage device 124. Moreover, the storage device 124 may include multiple media devices.

The exemplary client computing device 120 may alternatively be implemented such that the same hardware components that implement the memory 123 also implement the storage device 124. For example, the exemplary client computing device 120 may be implemented with memory chips that implement both the functionality of the memory 123 and the storage device 124. Many special purpose computing devices such as handheld computing devices (e.g. Palm Pilots) and Internet enabled cellular phones which could be used to implement the client computing device 120 are implemented in such a manner.

The network interface 125 of the exemplary client computing device 120 generally operably couples the exemplary client computing device 120 to the network 150 such that the client computing device 120 may communicate with the server computing device 110 via the network 150. To this end, the network interface 125 of the exemplary embodiment comprises an analog modem for use over POTS telephone lines such as a 28.8K or 56K modem, or a digital modem such as a Cable modem for use over a cable distribution network, an ISDN modem for use over an ISDN telephone line, or a DSL modem for use over a DSL telephone line. However, the network interface 118 may alternatively, or in addition, include a network interface controller such as an Ethernet controller or Token Ring controller that can be used to connect the client computing device 120 to the network 150 via a local area network, firewall, gateway, and/or router.

As shown, the exemplary client computing device 120 further includes the device interface 126. The device interface 126 is generally operable to establish a physical communications link 140 between the client computing device 120 and the medical device 130. To this end, the device interface 126 of the exemplary client computing device 120 includes a standard RS-232 serial port to which the medical device 130 may be operably coupled via an RS-232 cable.

However, the device interface 126 may alternatively, or in addition, include other communications mechanisms such as a parallel port, a SCSI port, a USB port, a 1394 port (i.e. FireWire or I-Link port), a Fibre Channel port, a network interface controller, or some other type of communications port to which a user may couple a corresponding communications port of the medical device 130 via an appropriate cable or connector. The device interface 126 may alternatively, or in addition, include wireless technologies such as RF and/or IR transmitter/receivers to establish the physical communications link 140 between the client computing device 120 and the medical device 130.

As depicted, the client computing device 120 includes one or more user I/O devices 127. The user I/O devices 127 in general provide a user of the client computing device 120 with mechanisms for entering information into the client computing device 120, receiving information from the client computing device 120, and/or controlling the operation of the client computing device 120. For example, the user I/O devices 127 may include cathode ray tubes (CRT), liquid crystal displays (LCD), light emitting diodes (LED), printers, and/or other output devices that are operable to visually present information to a user of the exemplary client computing device 120. The user I/O devices 127 may also include sound cards, wave generators, sequencers, mixers, speakers, and/or other audio devices that are used to audibly present information to a user of the exemplary client computing device 120.

Further, the user I/O devices 127 may include a mouse, a keyboard, a touch pad, a push button, a scanner, a stylus, a touch screen, and/or other input devices that provide a user of the exemplary client computing device 120 with an interface to directly control the operation of the exemplary client computing device 120 and/or indirectly control the operation of the server computing device 110 and the medical device 130.

The system bus 128 is generally operable to interconnect the processor 122, the memory 123, the storage device 124, the network interface 125, the device interface 126, and the user I/O devices 127. To this end, the system bus 128 in the exemplary embodiment includes bus lines and/or traces which enable the various components of the exemplary client computing device 120 to communicate with one another. Furthermore, the system bus 128 may be implemented with one or more buses utilizing one or more bus architectures such as PCI, ISA, and VME.

As shown, the system 100 further includes a medical device 130. The medical device 130 of the system 100 is generally operable to monitor one or more biological/physiological conditions and communicate with the client computing device 120 via the physical communications link 140 established between the client computing device 120 and the medical device 130. In an exemplary embodiment, the medical device 130 includes a glucose meter such as the glucose meters manufactured by Roche Diagnostics Corporation which are generally operable to measure blood glucose levels of blood applied to test strips. While the medical device 130 of the exemplary embodiment includes a glucose meter, the medical device 130 could be implemented to monitor and/or analyze other biological/physiological parameters or conditions such as body fluids or bodily functions (e.g. blood, urine, saliva), bodily signals (e.g. electrocardio-signals, brain waves, blood pressure waves), and/or other bodily stimuli (e.g. respiration) to obtain measurements of blood pressure, blood gases, blood coagulation, electrolytes, cardiovascular activity, drug levels, respiration rate, stress, etc.

As can be seen from FIG. 1, the exemplary medical device 130 includes a processor 132, memory 133, a communications interface 136, one or more user I/O devices 137, and a system bus 138. The processor 122 of the exemplary medical device 130 includes a single microprocessor or microcontroller; however, the processor 122 may alternatively include more than one processor. As a result of executing the software and/or firmware routines of the memory 133, the processor 132 controls the general operation of the medical device 130. More specifically, the processor 132 as a result of executing software and/or firmware routines of the memory 133 is generally operable to configure the medical device 130 to obtain measurement data indicative of a biological/physiological condition.

Further, the processor 132 as a result of executing the software and/or firmware routines of the memory 133 is generally operable to control communication between the client computing device 120 and the medical device 130 in accordance with a particular communications protocol which may be specific to the medical device 130. In an exemplary embodiment, the system 100 supports several different models and/or types of medical devices 130 which may use different communications protocols. In general, these different models and/or types of medical devices 130 may utilize protocols that define different procedures for formatting data and the procedure used to transfer the data. For example, different medical devices 130 may utilize (i) a different message or packet format, (ii) a different transfer rate, (iii) a different error detection scheme, (iv) a different error correction scheme, (v) a different command set, and/or (vi) a different compression scheme to name a few.

The memory 133 of the exemplary medical device 130 is operable to store data and instructions used by the processor 132. To this end, the memory 133, in an exemplary embodiment, includes random access memory for storing data, software instructions, and/or other information needed by the processor 132. However, the memory 133 may alternatively include other volatile memory types such as DRAM, SDRAM, and SRAM for storing data and software instructions and/or non-volatile memory such as ROMs, PROMs, EEPROMs, and flash memory for storing data and firmware instructions.

As shown, the exemplary medical device 130 further includes the communications interface 136. The communications interface 136 is generally operable to establish the physical communications link 140 between the client computing device 120 and the medical device 130. To this end, the communications interface 136 of the exemplary medical device 130 includes a standard RS-232 serial port to which the client computing device 120 may be operably coupled via an RS-232 cable.

The communications interface 136, however, may alternatively, or in addition, include other communications mechanisms such as a parallel port, a SCSI port, a USB port, a 1394 port (i.e. FireWire or I-Link port), a Fibre Channel port, a network interface controller, or some other type of communications port to which a user may couple a corresponding communications port of the client computing device 120 via an appropriate cable or connector. The communications interface 136 may alternatively, or in addition, include wireless technologies such as RF and/or IR transmitter/receivers to establish the physical communications link 140 between the client computing device 120 and the medical device 130.

The medical device 130 further includes one or more user I/O devices 137. The user I/O devices 137 in general provide a user of the medical device 130 with mechanisms for entering information into the medical device 130, receiving information from the medical device 130, and/or controlling the operation of the medical device 130. For example, the user I/O devices 137 may include cathode ray tubes (CRT), liquid crystal displays (LCD), light emitting diodes (LED), printers, and/or other output devices that are operable to visually present information to a user of the exemplary medical device 130. The user I/O devices 137 may also include sound cards, wave generators, sequencers, mixers, speakers, and/or other audio devices that are used to audibly present information to a user of the exemplary medical device 130.

Further, the user I/O devices 137 of the medical device 130 may include a mouse, a keyboard, a touch pad, a push button, a scanner, a stylus, a touch screen, and/or another input device that provides a user of the exemplary medical device 130 with an interface to directly control the operation of the exemplary medical device 130. The medical device 130 may also be implemented with no user I/O devices 137, and simply leverage the user I/O devices 127 of the client computing device 120. However, even a medical device 130 that highly leverages the user I/O devices 127 of the client computing device 120 will usually still have a few user I/O devices 137 such as an LED that provides visual feedback that the medical device 130 is powered, an LED that provides visual feedback that the physical communications link 140 has been established, and/or a button or switch to power the medical device 130 on or off.

The system bus 138 is generally operable to interconnect the processor 132, the memory 133, the communications interface 136, and the user I/O devices 137. To this end, the system bus 138 in the exemplary embodiment includes bus lines and/or traces which enable the various components of the medical device 130 to communicate with one another. Furthermore, the system bus 138 may be implemented with one or more buses utilizing one or more bus architectures such as PCI, ISA, VME, and PC-104.

As depicted in FIG. 1, the network 150 of the exemplary system 100 operably couples the client computing device 120 to the server computing device 110. The network 150 may illustratively include multiple public or private LANs and/or WANs (not shown) that are operably coupled to one another via routers, switches, hubs, gateways, proxies, and/or firewalls (not shown). In an exemplary embodiment, the network 150 utilizes the Internet to provide ubiquitous access to the server computing device 110 from the client computing devices 120.

Referring now to FIG. 2, a functional block diagram illustrates the interaction of data and functional components of the exemplary system 100. In general, the functional components depicted in FIG. 2 are implemented with software and/or firmware that is executed by the server computing device 110 and the client computing device 120. While the functional components of FIG. 2 are implemented via software and/or firmware and are so described below, those skilled in the art may elect to implement all or portions of the functional components with discrete analog circuit components, discrete digital circuit components, integrated analog circuits, integrated digital circuits, and/or integrated analog/digital hybrid circuits without undue experimentation and such implemented functional components may replace all or a portion of the hardware components illustrated in FIG. 1.

As illustrated, the exemplary server computing device 110 includes a server transport agent 202, protocol components 204, device data 206, patient data 208, and device identification components 214. Furthermore, the exemplary client computing device 120 includes a user interface 210, a client transport agent 212, a device identification component 214, an update component 216, and a protocol component 204.

The server transport agent 202 and the client transport agent 212 respectively configure the server computing device 110 and the client computing device 120 for communication therebetween via the network 150. In an exemplary embodiment, the server transport agent 202 and the client transport agent 212 configure the server computing device 110 and client computing device 120 to utilize the HTTP (hypertext transport protocol) over the TCP/IP network protocol. To this end, the server transport agent 202 of the exemplary embodiment comprises an HTTP server that is operable to receive HTTP requests from one or more client computing devices 120 and provide the client computing devices 120 with the requested information. The server transport agent 202 may include any one of a number of currently available HTTP servers or web application servers such as the Internet Information Server available from Microsoft Corporation, the Apache HTTP Server available from the Apache Group, and the Zope web application server available from Digital Creations, Inc. The server transport agent 202 may support other transport protocols such as FTP, TFTP, SMTP, etc. or other network protocols such as UDP, SMB, NetBUI, etc. in addition to or instead of the HTTP protocol and the TCP/IP protocols.

As illustrated, the server computing device 110 comprises several protocol components 204 that when transferred to a client computing device 120 configure the client computing device 120 to use a particular communications protocol when communicating with an identified medical device 130. As indicated above, the exemplary system 100 supports medical devices 130 which utilize different communications protocols. Accordingly, the server computing device 110 maintains protocol components 204 which when executed by the client computing device 120 cause the client computing device 120 to communicate with a medical device 130 in the proper communications protocol for the medical device 130. To this end, the exemplary server computing device 110 maintains a separate protocol component 204 for each type of medical device 130 that the system 100 supports.

The server computing device 110 may alternatively include protocol components 204 that support more than one communications protocol or that can configure the client computing device 130 to communicate with more than one type of medical device 130. While including multiple functionality into a single protocol component 204 reduces the number of protocol components 204 that the server computing device 110 needs to maintain, these multi-functional protocol components 204 are also likely to be larger in size than a protocol component 204 that merely implements a communications protocol for a single type of medical device 130. A larger protocol component 204 takes longer to transfer to the client computing device 120; however, a client computing device 120 that is used with several types of medical devices 130 may more than recoup this transfer time by not needing to download as many protocol components 204 from the server computing device 110.

In the exemplary embodiment, the protocol components 204 are implemented as ActiveX components which can be downloaded and executed by the client computing device 120 via a web browser. However, the protocol components 204 may also be implemented using other software technologies such as COM, DCOM, Java, JavaScript, VBScript, Perl, Python, as well as native applications written in the language of the developers choice which could be executed on the client computing device 120 via various RPC techniques. Furthermore, by utilizing interpreted languages such as JavaScript and VBScript or byte compiled languages such as Java, Perl, and Python, the server computing device 110 may maintain a single version of a protocol component 204 or a small number of versions of a particular protocol component 204 in order to support a wide range of client computing device platforms (i.e. hardware and operating system combinations.) In other words, the server computing device 110 may be efficiently implemented to supported a wide range of client computing devices 110 (e.g. computer systems using the McIntosh, Windows, and/or Linux operating systems, Palm Pilots, Handspring Visors, Internet enabled cellular phones, etc.).

As illustrated in FIG. 2, the server computing device 110 also includes device data 206 and patient data 208 stored in the memory 114 and/or the storage device 116. The device data 206 generally includes information regarding types of medical devices 130 that the system 100 supports and which of the protocol components 204 supports a certain medical device 130. The server computing device 110 utilizes the device data 206 to determine which of the protocol components 204 is the proper protocol component 204 for a given medical device 130 so that the proper protocol component 204 is transferred to the client computing device 120 if needed.

The patient data 208 generally includes biological and/or physiological data collected from patients being monitored by the system 100. Moreover, the patient data 208 may further include patient identification information (e.g. name, date of birth, address, etc) and authentication information (e.g. username/password, web cookie text, client computing device address, medical device serial number, client computing device network address, etc.) which may be used to verify the identify of a given patient and/or correlate a given patient with prior biological/physiological data collected by the server computing device 110. The system 100 may also allow anonymous access in which case the server computing device 110 may maintain no patient data or may maintain patient data in an anonymous manner that still enables a patient to obtain their collected biological/physiological data. Anonymous access enables a patient to retrieve, view, and/or analyze the current biological/physiological data of the medical device 130 without fear of someone tying the data to the patient.

The user interface 210 of the client computing device 120 is generally operable to provide a user (e.g. a patient, nurse, physician, etc.) with a mechanism for controlling operation of the system 100 in regard to the client computing device 120 and the medical device 130. More specifically, the user interface 210 of the exemplary embodiment is operable to display HTML (hyper-text markup language) documents and HTML forms. However, the user interface 210 could display information in other formats such RTF, PDF, and ASCII Text or other markup language formats such as SGML, XML, Tex, and/or LaTeX.

In an exemplary embodiment, the user interface 210 and the client transport agent 212 described above are implemented with a standard web browser such as Internet Explorer available from Microsoft Corporation of Redmond, Wash. or Netscape Communicator available from Netscape Communications Corporation of Mountain View, Calif. and the TCP/IP protocol portion of the client transport agent 212 is implemented with the TCP. These standard web browsers among other things are operable to send and receive packets of information that conform to the HTTP and the TCP/IP protocols, send requests for HTML documents, receive HTML documents, display HTML documents, and send data that a user has input into a HTML form.

Alternatively, the user interface 210 may be implemented as a native custom application of the client computing device 120 that is specifically designed for the system 100. The custom application could be implemented to display HTML and other markup language documents in a manner similar to a standard web browser. However, the custom application is more likely to be implemented to receive information from the server computing device 110 in a non-markup language format, and display the information via a customized graphical interface.

The device identification component 214 of the exemplary client computing device 120 generally causes the client computing device 120 to identify the medical device 130 without the need for the user to enter identifying information for the medical device 130. To this end, the device identification component 214 in an exemplary embodiment scans a predetermined port of the client computing device 120 to determine the type of medical device 130 operably coupled to the predetermined port. The exact procedure that the device identification component 214 utilizes to identify the medical device 130 operably coupled to the client computing device 120 depends upon the communications protocols utilized by the medical devices supported by the system 100. Several known techniques may be used such as identifying the medical device 130 based upon (i) responses received from the medical device 130 due to stimulus signals applied to the medical device 130, (ii) identification codes retrieved from the medical device 130, (iii) serial numbers retrieved from the medical device 130, and/or (iv) other information retrieved from the medical device 130. It is understood that device identification component 214 may include a manual device identification such as a drop down box, check box, or other manual entry.

Besides merely scanning a predetermined port for the medical device 130, the device identification component 214 may allow a user to specify via the user interface 210 to which port the medical device 130 is operably coupled. Further, the identification component 214 could simply scan all ports of a particular type (e.g. all USB ports, all SCSI ports, all parallel ports, wireless interfaces, etc) or scan a user-definable set of ports.

In an exemplary embodiment, the device identification component 214 comprises an executable program or script which when executed by the client computing device 120 generally causes the client computing device 120 to identify the medical device 130 as described above. The device identification component 214 may alternatively comprise hardware, firmware, or a combination of hardware, firmware, and/or software that configure the client computing device 120 to identify the medical device 130.

The update component 216 in general ensures that the client computing device 120 utilizes the proper protocol component 204 for the identified medical device 130. To this end, the update component 216 in an exemplary embodiment generally determines which protocol components 204 (if any) are currently stored in the memory 123 and/or the storage device 124 of the client computing device 120 and whether any of the protocol components 204 of the client computing device 120 is the proper protocol component 204 for the identified medical device 130. If the update component 216 determines that client computing device 120 does not have a copy of the proper protocol component 204 for the identified medical device 130, then the update component 216 operates in conjunction with the client transport agent 212 to obtain a copy of the correct protocol component 204 from the server computing device 110.

While the update component 216 could be implemented as a separate software, firmware, and/or hardware component, the update component 216 in an exemplary embodiment is implemented with the standard web browser that is also used to implement the user interface 212 and transport agent 214 of the client computing device 120. Web browsers generally provide mechanisms which enable remote computer systems such as the server computing device 110 to cause the client computing device 120 to execute software routines. For example, many web browsers support execution of Java Applets, JavaScript, ActiveX Controls, and other types of software technologies by which the server computing device 110 can cause the client computing device 130 to execute software in response to information received from the server computing device 110.

Moreover, web browsers generally also include the ability to determine whether a particular software component such as an ActiveX Control, a plug-in application, or a Java Applet is already installed on the client computing device 120 in response to information received from a server computing device 110. Further, web browsers generally also include the ability to determine the version of such installed software components. Web browsers also generally include the ability to download and install via the client transport agent 212 a needed software component such as an ActiveX Control, a plug-in application, or a Java Applet from the server computing device 110 in response to information received from the server computing device 110.

Moreover, web browsers also generally include the ability to cache information received from a server computing device 110 and determine whether the information in the cache is up-to-date with corresponding information of the server computing device 110. In this manner, the web browser of the client computing device 120 can prevent the repetitive transfer of the same information from the server computing device 110 to the client computing device 120. In other words, if the client computing device 120 requests a particular resource from the server computing device 110 and the client computing device 120 already has a copy of that resource in the cache, then the web browser can cause the client computing device 120 to use the cached version of the resource, thus eliminating a transfer of the resource from the server computing device 110 to the client computing device 120.

As indicated above, the protocol components 204 generally configure the client computing device 120 to use a particular communications protocol when communicating with an identified medical device 130. The exemplary system 100 supports medical devices 130 which utilize different communications protocols. Accordingly, the server computing device 110 maintains protocol components 204 which when executed by the client computing device 120 cause the client computing device 120 to communicate with a medical device 130 in the proper communications protocol for the medical device 130. In an exemplary embodiment, the protocol components 204 comprise software such as Java Applets, JavaScripts, ActiveX Controls, etc. which is executed by the client computing device 130 in response to information received from the server computing device 110.

Figure 3:
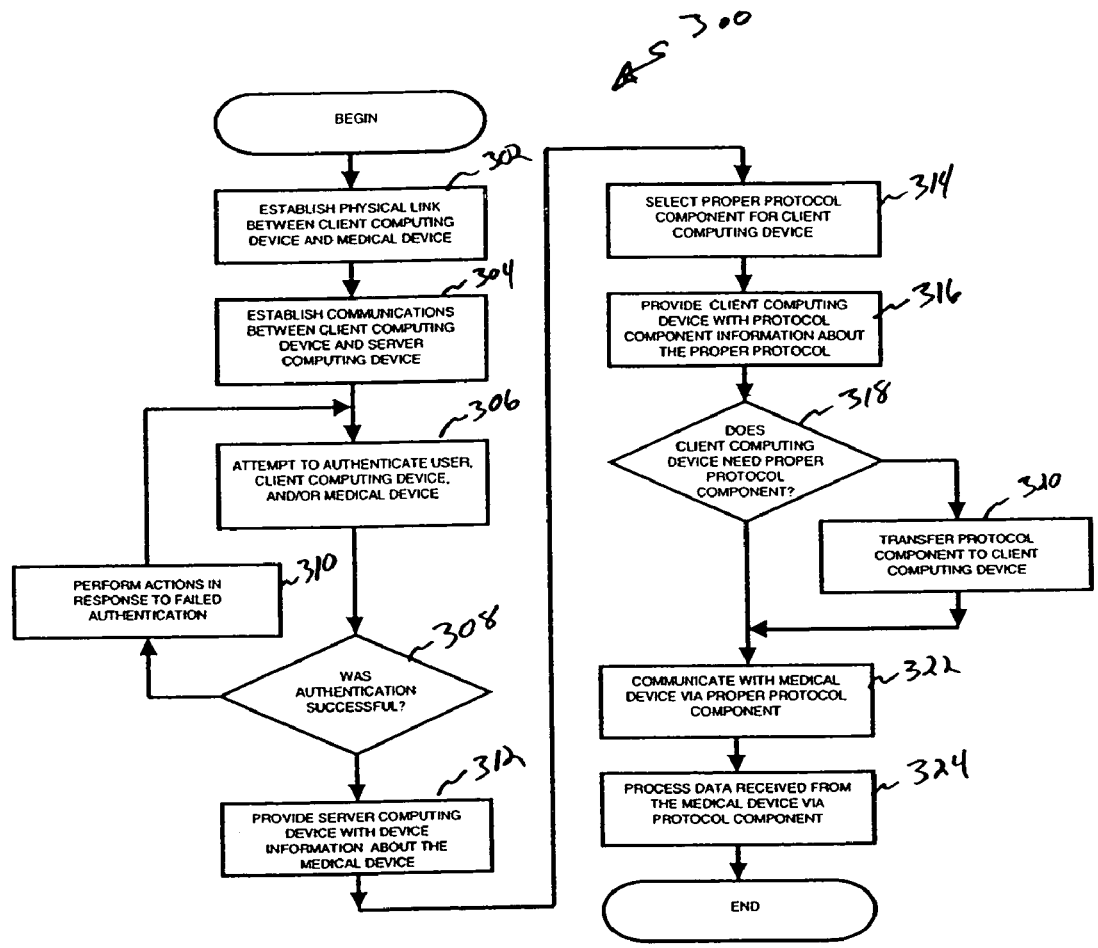
FIG. 3 is a flowchart illustrating an exemplary method of operation for the system of FIG. 1.

A flowchart depicting an exemplary method of operation 300 is illustrated in FIG. 3. As illustrated, the exemplary method 300 begins in step 302 with establishing a physical communications link 140 between the client computing device 120 and the medical device 130. In an exemplary embodiment, a user of the system establishes the physical communications link 140 by coupling a interface cable between a port (e.g. serial I/O port) of the medical device 130 and a corresponding port (e.g. COM port 1) of the client computing device 120. However, if the medical device 130 includes a wireless communication mechanism such as IR and/or RF transmitters/receivers, then the physical communications link 140 is established by simply placing the medical device 130 within transmission range of the corresponding IR and/or RF transmitters/receivers of the client computing device 120.

In step 304 of the exemplary method 300, the client computing device 120 establishes communications with the server computing device 110. In an exemplary embodiment, the client computing device 120 establishes communications with the server computing device 110 in response to a user requesting via the user interface 210 that the client transport agent 212 establish communications with the server computing device 110. In particular, the user in the exemplary embodiment requests via a web browser of the user interface 210 that the web browser connect to the server computing device 110 and associated transport agent 202 identified by a particular URI (Universal Resource Identifier), URL (Universal Resource Locator), PURL (Persistent Uniform Resource Locator) and/or URN (Universal Resource Name).

The server computing device 110 in step 306 attempts to authenticate the user, the client computing device 120, and/or the medical device 130. In an exemplary embodiment, the server computing device 110 attempts to authenticate the user, the client computing device 120, and/or the medical device 130 via various authentication schemes in order to enable a user to retrieve previously collected biological/physiological data, and/or ensure that collected biological/physiological data is kept private. In an exemplary embodiment, the user via the user interface 210 enters a username and password which the server computing device 110 compares to username/password pair of the maintained patient data 208 to determine whether the user has entered a valid username/password pair. However, in environments where security/privacy is not a concern, an alternative embodiment of the server computing device 110 does not authenticate the user, the client computing device 120, and/or the medical device 130. It should be appreciated that other authentication methods are also suitable. For example, authentication may be based further upon or alternatively upon the network address of client computing device 120, the serial number of the medical device 130, stored authentication keys (e.g. PGP keys), etc.

In step 308, the server computing device 110 determines whether the attempt to authenticate the user, the client computing device 120, and/or the medical device 130 succeeded. In an exemplary embodiment in which the server computing device 110 utilizes username/password pairs for authentication, the server computing device 110 determines that the authentication attempt failed if the received username/password pair is invalid. In step 310, the server computing device 110 performs various other actions in response to receiving an invalid username/password pair such as logging the invalid username/password pair, logging the network address of the client computing device 120, blocking connections from the client computing device 120 if a threshold number of attempts is exceeded, etc. After performing the various action of step 308, the server computing device 110 returns to step 306 in order to re-attempt to authenticate the user, the client computing device 120, and/or the medical device 130.

The device identification component 214 of the client computing device 120 in step 312 provides the server computing device 110 with device information from which the server computing device 110 determines the proper protocol component 204 to be used with the medical device 130. As indicated above, the device identification component 214 generally interrogates the medical device 130 via a series of signals, receives signals from the medical device 130 in response to the interrogation, and discerns the type of medical device 130 connected to the client computing device 120 based upon the signals received from the medical device 130. The signals received from the medical device 130 may include ACK signals or other signals indicative of information such as a serial number, model number, device type, version number, etc. At any rate, the device identification component 214 provides the server computing device 110 with device information via the client transport agent 212 from which the server computing device 110 ascertains the type of medical device 130 operably coupled to the client computing device 120.

The server computing device 110 then determines in step 314 the proper protocol component 204 to communicate with the identified medical device 130. In particular, the server computing device 10 in the exemplary embodiment utilizes the device data 206 and the device information received from the device identification component 214 to select the proper protocol component 204 for the client computing device 120 to use in communicating with the identified medical device 130.

The server computing device 110 in step 316 provides the update component 216 of the client computing device 120 with protocol component information that identifies the proper protocol component 204 to be used with the identified medical device 130. In an exemplary embodiment, the server computing device 110 merely transfers to the client computing device 120 an HTML document that includes a reference to the proper ActiveX Control for the client computing device 120 to execute in order to communicate with the medical device 130.

As result of receiving the protocol component information from the server computing device 110, the client computing device 120 in step 318 determines whether the client computing device 120 needs to receive a copy of the proper protocol component 204 from the server computing device 110. In an exemplary embodiment, the web browser of the user interface 210 processes an HTML document received from the server computing device 110 which causes the update component 216 to verify that the client computing device 120 already has a current version of the proper protocol component 204 referenced by the HTML document. If the update component 216 determines that the client computing device 120 already has the current version, then the client computing device 120 proceeds to step 312 in order to communicate with the medical device 130 via the protocol component 204.

If the client computing device 120 determines that the client computing device 120 needs a copy of the proper protocol component 204, then the client computing device 120 in step 320 receives a copy of the proper protocol component 204 from the server computing device 110. In particular, the client transport agent 212 in an exemplary embodiment retrieves a copy of the proper protocol component 204 from the location specified in an HTML document received from the server computing device 110.

The update component 216 of the client computing device 120 ensures that the client computing device 120 includes the proper protocol component 204 for the medical device 130. As a result, the client computing device 120 communicates with the medical device 130 utilizing the proper protocol component 204 even if the protocol component 204 is later revised and even if the client computing device 120 did not previously have the proper protocol component 204 for the medical device 130.

The client computing device 120 then in step 322 executes the proper protocol component 204 in order to transfer data and/or control information between the client computing device 120 and the medical device 130. In an exemplary embodiment, the client computing device 120 executes the proper protocol component 204 referenced by the HTML document received from the server computing device 110.

As a result of executing the proper protocol component 204, the client computing device 120 performs various operations in regard to communicating with the medical device 130 on the behalf of the client computing device 120 and/or the server computing device 110. For example, the server computing device 110 may cause client computing device 120 to issue commands to the medical device 130 via the protocol component 204 which cause the medical device 130 to adjust an internal clock, clear stored measurement data, retrieve stored measurement data, update calibration or other parameters used to obtain measurement data, perform a test to obtain measurement data, or other tasks.

Similarly, the server computing device 110 may cause the client computing device 120 to transfer measurement data, device status data, etc. from the medical device 130 to the server computing device 110. More specifically, the client computing device 120 obtains the data from the medical device 130 via the protocol component 204, and after completing the transfer of data from the medical device 130 to the client computing device 120, the client computing device 120 transfers the data to the server computing device 110. However, the client computing device 120 may alternatively begin the transfer of received data to the server computing device 110 before receiving all of the requested data from the medical device 130.

As indicated above, some of the operations performed on behalf of the server computing device 110 cause the client computing device 120 to provide the server computing device 110 with data such as measurement data, device status data, etc. Accordingly, the server computing device 110 in step 322 processes data received from the measurement device 130 via the client computing device 120. For example, the server computing device 110 in an exemplary embodiment stores measurement data received from the client computing device 120 with the patient data 208 such that the measurement data is associated with the user, client computing device 120, and/or medical device 130 authenticated in step 306. In this manner, the sever computing device 110 maintains historic measurement data for an authenticated user, client computing device 120, and/or medical device 130. In response to a request received from the client computing device 120, the server computing device 110 at later date retrieves and/or analyzes the historic data for the authenticated user, the client computing device 120, and/or the medical device 130. Further, the server computing device 110 provides the client computing device 120 with results data in the form of a HTML document that includes tables, charts, graphs, explanations, etc. to aid in assessing the meaning of the current measurement data and/or the historic measurement data.

Alternatively, the server computing device 110 simply analyzes the received measurement data and provides the client computing device 120 with results data that is representative of such analysis without storing the measurement data for future retrieval and analysis. In this manner, the server computing device 110 provides a user an anonymous mechanism for analyzing their current measurement data.

Figure 4:
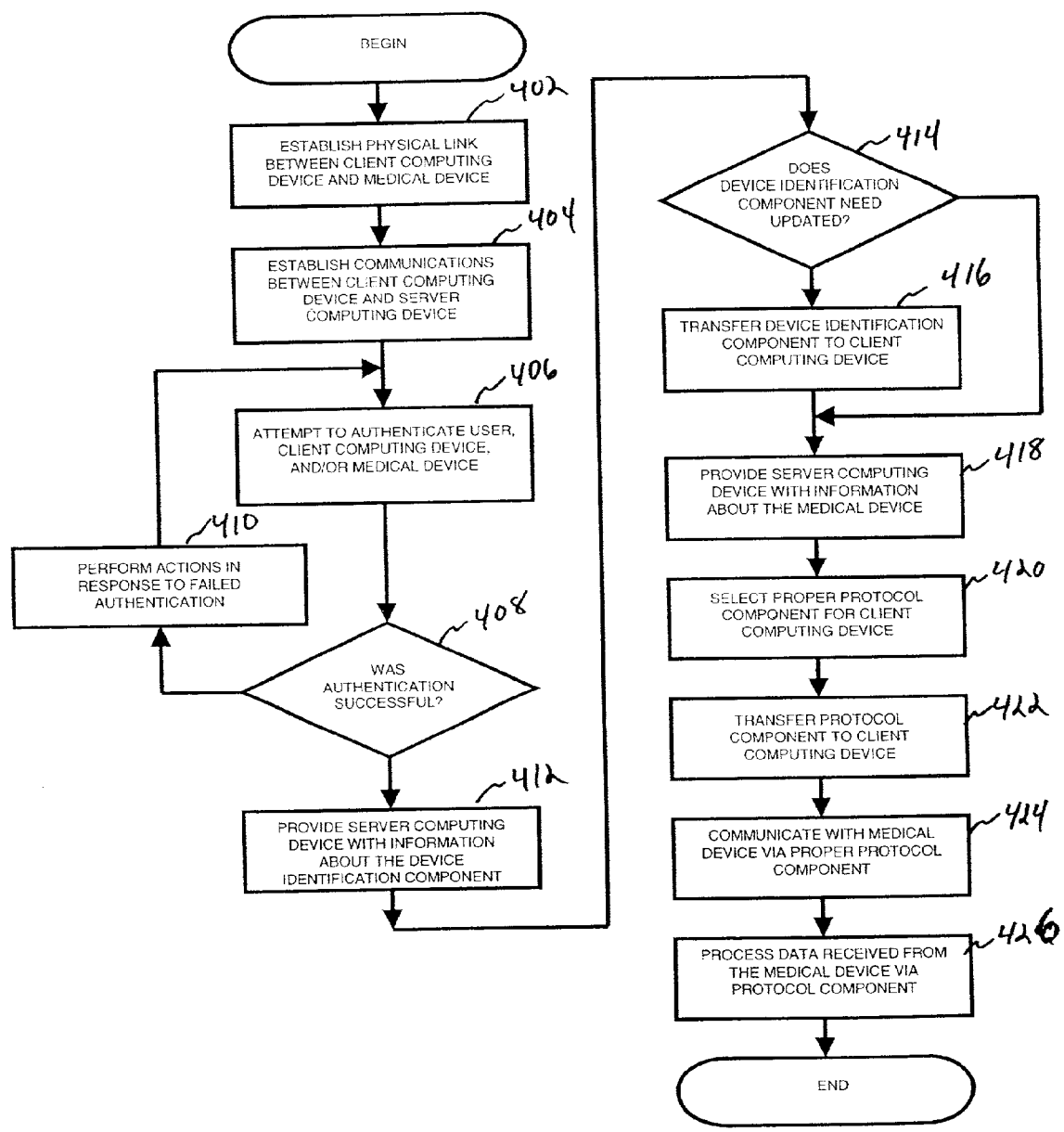
FIG. 4 is a flowchart illustrating another exemplary method of operation for the system of FIG. 1.

A flowchart depicting another exemplary method of operation 400 is illustrated in FIG. 4. As illustrated, the exemplary method 400 begins in step 402 with establishing a physical communications link 140 between the client computing device 120 and the medical device 130 as described above in regard to FIG. 3.

In step 404, the client computing device 120 establishes communications with the server computing device 110. In an exemplary embodiment, the client computing device 120 establishes communications with the server computing device 110 in response to a user requesting via the user interface 210 that the client transport agent 212 establish communications with the server computing device 110. In particular, the user in the exemplary embodiment requests via a web browser of the user interface 210 that the web browser connect to a particular server computing device 110 and associated transport agent 202 identified by a particular URI (Universal Resource Identifier), URL (Universal Resource Locator), PURL (Persistent Uniform Resource Locator) and/or URN (Universal Resource Name) which services medical devices 130 of a particular family or type. By utilizing different URLs for different models of medical devices 130, different types of medical devices 130, different classes of medical devices 130, and/or different manufacturers of medical devices 130, the URL essentially provides a mechanism to identify or partially identify the medical device 130 attached to the client computer system 120. For example, a first URL may be defined for a first model of glucose meters, a second URL may be defined for a class of glucose meters which have similar capabilities, and a third URL may be defined for all cholesterol meters of a certain manufacturer.

The server computing device 110 in step 406 attempts to authenticate the user, the client computing device 120, and/or the medical device 130 in a manner similar to step 306 of FIG. 3. In step 408, the server computing device 10 determines whether the attempt to authenticate the user, the client computing device 120, and/or the medical device 130 succeeded in a manner similar to step 308 of FIG. 3. In step 410, the server computing device 110 performs various other actions in response to receiving an invalid username/password pair such as logging the invalid username/password pair, logging the network address of the client computing device 120, blocking connections from the client computing device 120 if a threshold number of attempts is exceeded, etc and returns to step 406 in order to re-attempt to authenticate the user, the client computing device 120, and/or the medical device 130.

In step 412, the client computing device 120 provides the server computing device 110 with information from which the server computing device 110 may determine whether the client computing device 120 has an appropriate device identification component 214 for the medical device 130. For example, the client computing device 120 may provide the server computing device 110 with a version number, filename, byte length, checksum value, or other information about the current device identification component 214 (if any) of the client computer device 120.

From the information received from the client computing device 120 and data maintained by the server computing device 110, the server computing device 110 in step 414 determines whether to transfer an identification component 214 to the client computing device 120. In an exemplary embodiment, the server computing device 110 determines that an identification component 213 needs to be transferred to the client computing device 120 if the client computing device 120 does not have an identification component 214 for the type of medical device 130 attached to the client computing device 110, or if the identification component 214 of the client computing device 120 is not the latest version of the identification component 214 for the type of medical device 130 attached to the client computing device 120.

As described above in regard to steps 412 and 414, the client computing device 120 essentially provides the server computing device 10 with information from which the server computing device 110 determines the appropriateness of the identification component 214 of the client computing device 120. However, it should be appreciated that alternatively the server computing device 110 may provide the client computing device 120 with information from which the client computing device 120 determines for itself the appropriateness of the identification component 214 of the client computing device 120. In particular, the client computing device 120 may determine whether the identification component 214 of the client computing device 120 needs to be updated in a manner similar to steps 316 and 318 of FIG. 3.

If the server computing device 110 determines an identification component 214 is to be transferred to the client computing device 120, then the server computing device 110 in step 416 causes the identification component 214 to be transferred to the client computing device 120. As should be appreciated, the server computing device 110 utilizes various data transfer techniques to transfer the identification component 214 to the client computing device 120 such as FTP transfer, HTTP transfer, remote copy, etc. In particular, the server computing device 110 in an exemplary embodiment provides the web browser of the user interface 210 with an HTML document which when processed by the web browser causes the client computing device 120 to download and execute the identification component 214 from the server computing device 110 or another computing device.

In step 418, the client computing device 120 provides the server computing device 110 with device information from which the server computing device 110 determines the proper protocol component 204 to be used with the medical device 130. As indicated above, the device identification component 214 interrogates the medical device 130 via a series of signals, receives signals from the medical device 130 in response to the interrogation, and discerns the type of medical device 130 connected to the client computing device 120 based upon the signals received from the medical device 130. The signals received from the medical device 130 include ACK signals and/or other signals that are indicative of information such as a serial number, model number, device type, version number, etc. At any rate, the device identification component 214 provides the server computing device 110 with device information via the client transport agent 212 from which the server computing device 110 ascertains the type of medical device 130 operably coupled to the client computing device 120.

The server computing device 110 then determines in step 414 the proper protocol component 204 to communicate with the identified medical device 130. In step 416, the server computing device 110 causes the proper protocol component 204 to be used with the identified medical device 130 to be transferred to the client computing device 120. To this end, the server computing device 110 provides the client computing device 120 with a location from which the client computing device 120 downloads the proper protocol component 204. However, it should be appreciated that instead of the client computing device 120 downloading the information from the location identified by the server computing device 204, the server computing device 110 could alternatively upload the protocol component 204 to the client computing device 120 or causing another computing device to upload the protocol component 204 to the client computing device 120.

The client computing device 120 then in step 424 executes the proper protocol component 204 in order to transfer data and/or control information between the client computing device 120 and the medical device 130. As a result of executing the proper protocol component 204, the client computing device 120 performs various operations in regard to communicating with the medical device 130 on the behalf of the client computing device 120 and/or the server computing device 110. For example, the server computing device 110 may cause client computing device 120 to issue commands to the medical device 130 via the protocol component 204 which cause the medical device 130 to adjust an internal clock, clear stored measurement data, retrieve stored measurement data, update calibration or other parameters used to obtain measurement data, perform a test to obtain measurement data, or other tasks.

Similarly, the server computing device 110 may cause the client computing device 120 to transfer measurement data, device status data, etc. from the medical device 130 to the server computing device 110. Accordingly, the server computing device 110 in step 426 processes data received from the measurement device 130 via the client computing device 120 in a manner similar to step 324 of FIG. 3.

Figure 5:
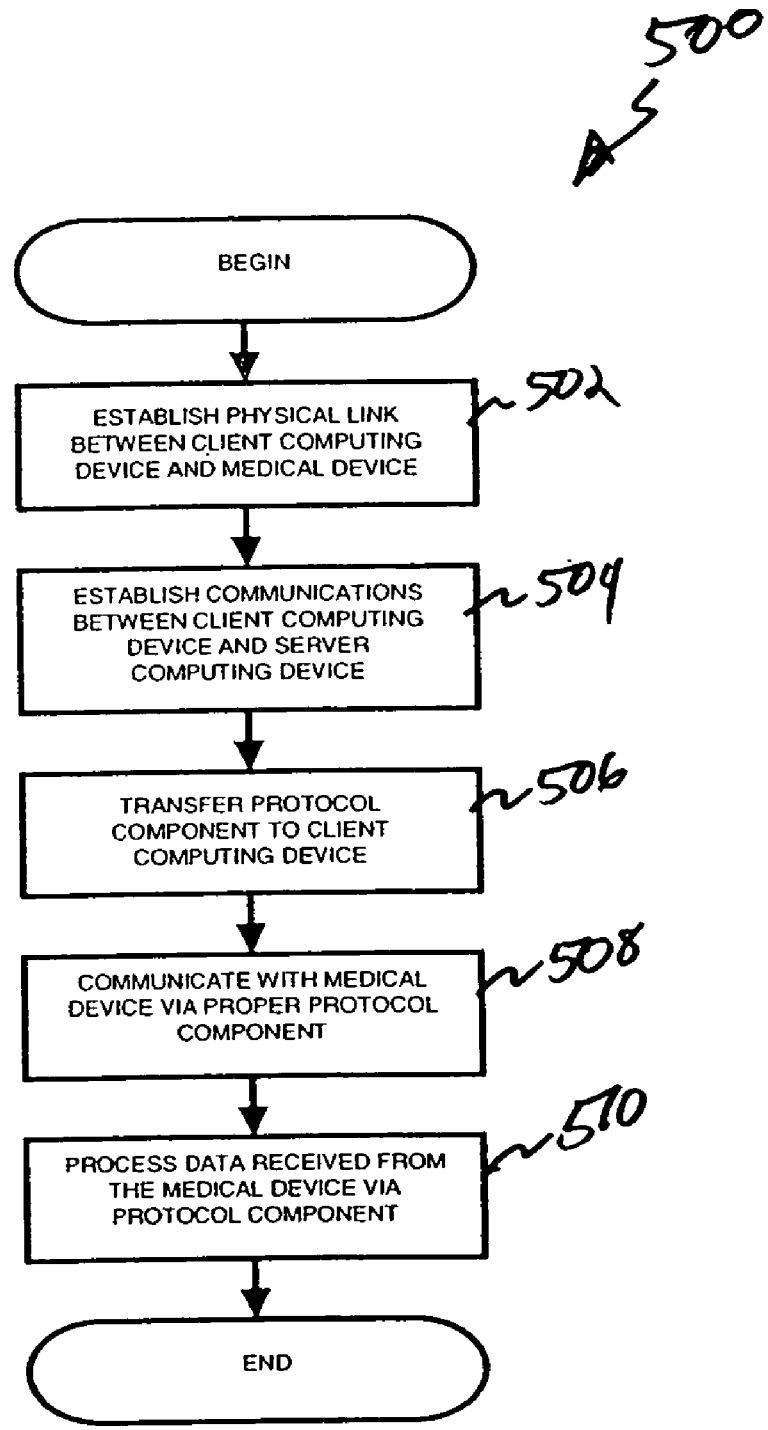
FIG. 5 is a flowchart illustrating yet another exemplary method of operation for the system of FIG. 1.

A flowchart depicting yet another exemplary method of operation 500 is illustrated in FIG. 5. As illustrated, the exemplary method 400 begins in step 502 with establishing a physical communications link 140 between the client computing device 120 and the medical device 130 as described above in regard to FIG. 3.

In step 504, the client computing device 120 establishes communications with the server computing device 110. In an exemplary embodiment, the client computing device 120 establishes communications with the server computing device 10 in response to a user requesting via the user interface 210 that the client transport agent 212 establish communications with the server computing device 110. In particular, the user in the exemplary embodiment requests via a web browser of the user interface 210 that the web browser connect to a particular server computing device 110 and associated transport agent 202 identified by a particular URI (Universal Resource Identifier), URL (Universal Resource Locator), PURL (Persistent Uniform Resource Locator) and/or URN (Universal Resource Name) which services medical devices 130 of a particular model, class, and/or manufacturer. By utilizing different URLs for different models, different types, different classes, and/or different manufacturers of medical devices 130, the URL essentially provides a mechanism to identify or partially identify the medical device 130 attached to the client computer system 120. For example, a first URL may be defined for a first model of glucose meters, a second URL may be defined for a class of glucose meters which have similar capabilities, and a third URL may be defined for all cholesterol meters of a certain manufacturer.

In an exemplary embodiment, the client computing device 120 in step 504 provides the user of the medical device 130 with a list of medical device from which to select the model, type, class, and/or manufacturer of the medical device 130 coupled to the client computing device 120. In the exemplary embodiment, the list of medical devices 130 is defined by a HTML document comprising hyper-links which when selected cause the client computing device 120 to establish communications with the server computing device 110 via the proper network location (e.g. URL) for the medical device 130. The list of medical devices 130 may alternatively or in addition to be presented as one or more drop-down lists from which the user may select the model, type, class, and/or manufacturer of the medical device 130. Furthermore, the list of medical devices 130 may be presented to the user via an application program that enables the user to select the model, type, class, and/or manufacturer of the medical device 130 via drop-down lists, check-boxes, radio-buttons, text entry forms, and/or other data input mechanisms and that determines the proper network location (e.g. URL) from the received information.

In step 506, the server computing device 110 causes the proper protocol component 204 to be used with the identified medical device 130 to be transferred to the client computing device 120. It should be appreciated that the client computing device 120 has essentially identified the model, type, class, and/or manufacturer of the medical device 130 in step 504 via the particular URI, URL, PURL, and/or URN. Accordingly, the server computing device 110 as a result of establishing communications with the client computing device 120 via the URI, URL, PURL, and/or URN provides the client computing device 120 with a location from which the client computing device 120 downloads the protocol component 204 for the model, type, class, and/or manufacturer of the medical device 130. However, it should be appreciated that instead of the client computing device 120 downloading the information from the location identified by the server computing device 204, the server computing device 110 could alternatively upload the protocol component 204 to the client computing device 120 or cause another computing device to upload the protocol component 204 to the client computing device 120.

The client computing device 120 then in step 508 executes the proper protocol component 204 in order to transfer data and/or control information between the client computing device 120 and the medical device 130. As a result of executing the proper protocol component 204, the client computing device 120 performs various operations in regard to communicating with the medical device 130 on the behalf of the client computing device 120 and/or the server computing device 110. For example, the server computing device 110 may cause client computing device 120 to issue commands to the medical device 130 via the protocol component 204 which cause the medical device 130 to adjust an internal clock, clear stored measurement data, retrieve stored measurement data, update calibration or other parameters used to obtain measurement data, perform a test to obtain measurement data, or other tasks.

Similarly, the server computing device 110 may cause the client computing device 120 to transfer measurement data, device status data, etc. from the medical device 130 to the server computing device 110. Accordingly, the server computing device 110 in step 510 processes data received from the measurement device 130 via the client computing device 120 in a manner similar to step 324 of FIG. 3.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention are desired to be protected. For example, exemplary methods of operation have been described as a series of sequential steps. However, it should be appreciated that certain steps of the exemplary methods of operation may occur in parallel or pseudo-parallel. Moreover, it should be appreciated that the order of steps is merely exemplary and embodiments of the invention may execute steps in a different order than the ones depicted. Furthermore, it should be appreciated that embodiments of the invention may combine steps from one or more of the exemplary methods depicted in FIGS. 3–5 and that embodiments of the invention are not required to include all of the steps of one of the exemplary methods depicted in FIGS. 3–5.

What is claimed is:

1. A first computing device for accessing a medical device operably coupled to a second computing device via a network, the first computing device comprising:
  a storage device comprising a plurality of protocol components that configure the second computing device to communicate with a plurality of medical devices in accordance with communications protocols supported by the plurality of medical devices;
  a memory comprising a plurality of instructions;

a network interface adapted to communicate with the second computing device via the network; and a processor operably coupled to the storage device, the memory, and the network interface and adapted to execute the plurality of instructions to cause the processor
- to receive from the second computing device via the network interface identification information from which a medical device type of the medical device coupled to the second computing device is determined,
- to provide protocol component information to the second computing device via the network interface which identifies the protocol component from the plurality of protocol components for the second computing device to use to communicate with the medical device, and
- to receive measurement data from the medical device via the network interface in response to the second computing device communicating with medical device via the protocol component identified by the protocol component information.

2. The first computing device of claim 1, wherein the plurality of instructions, when executed by the processor, further causes the processor to transfer the protocol component identified by the protocol component information to the second computing device via the network interface prior to receiving the measurement data.

3. The first computing device of claim 1, wherein the plurality of instructions, when executed by the processor, further causes the processor to transfer to the second computing device via the network interface, the protocol component identified by the protocol component information if the second computing device does not have a copy of the protocol component identified by the protocol component information.

4. The first computing device of claim 1, wherein the plurality of instructions, when executed by the processor, further causes the processor to receive authentication information from the second computing device via the network interface, and store the measurement data received from the medical device in the storage device such that the measurement data is associated with any previously received data associated with the authentication information.

5. The first computing device of claim 1, wherein the plurality of instructions, when executed by the processor, further causes the processor to analyze the measurement data received from the medical device to obtain results data in a markup language format, and provide the second computing device via the network interface with the results data in the markup language format.

6. The first computing device of claim 1, wherein the plurality of instructions, when executed by the processor, further causes the processor to receiving measurement data from the medical device via the network interface that is indicative of at least one blood glucose measurement.

* * * * *